United States Patent

Adams

Patent Number: 5,846,201
Date of Patent: Dec. 8, 1998

[54] ELEVATION PLANE FOCUSING IN AN ULTRASOUND IMAGING SYSTEM

[75] Inventor: Darwin P. Adams, Lexington, Mass.

[73] Assignee: Hewlett-Packard Company, Palo Alto, Calif.

[21] Appl. No.: 912,179

[22] Filed: Aug. 15, 1997

[51] Int. Cl.$^6$ .................................................. A61B 8/00
[52] U.S. Cl. ............................................................ 600/447
[58] Field of Search .................................. 600/447, 459; 73/625–626; 128/916; 367/105

[56] References Cited

U.S. PATENT DOCUMENTS

| | | | |
|---|---|---|---|
| 5,027,820 | 7/1991 | Pesque | 128/916 X |
| 5,301,168 | 4/1994 | Miller . | |
| 5,349,262 | 9/1994 | Grenon et al. . | |
| 5,462,057 | 10/1995 | Hunt et al. | 600/447 |
| 5,490,512 | 2/1996 | Kwon et al. | 600/447 |
| 5,563,346 | 10/1996 | Bartelt et al. | 600/447 |
| 5,579,770 | 12/1996 | Finger | 600/447 |
| 5,582,177 | 12/1996 | Hanafy et al. . | |
| 5,655,536 | 8/1997 | Takamizawa | 600/447 |
| 5,671,746 | 9/1997 | Dreschel et al. | 600/447 |

*Primary Examiner*—Francis J. Jaworski
*Attorney, Agent, or Firm*—Mark Z. Dudley

[57] ABSTRACT

An ultrasound imaging system includes an array of ultrasound transducer elements, wherein the transducer array is divided into plural transducer elements arranged in the direction of a scan plane and each transducer element is divided into three or more segments in the direction of an elevation plane. Also included are a transmitter for transmitting ultrasound energy into a region of interest from the array, a receiver for receiving signals generated by the array in response to the ultrasound echoes, a signal processing section including a signal processing circuit, a beam former, and a controller. The signal processing section is operable for effecting system control and for effecting signal processing and image display, and in particular, for allocating the channels with respect to the segments to vary the arrangement of signal processing channels applied to selected segments wherein the allocation is performed according to beam focal length. The system optimizes the channel allocation for improved electronic focusing in the scan plane and the elevation plane.

10 Claims, 3 Drawing Sheets

ELEVATION PLANE FOCUSING IN AN ULTRASOUND IMAGING SYSTEM

FIELD OF THE INVENTION

The invention generally relates to ultrasonic imaging and more particularly to electronic focusing of a transducer array operable in an ultrasonic imaging system.

BACKGROUND OF THE INVENTION

Ultrasonic imaging systems are known for detecting or imaging the internal structures of liquid, solid, and semi-solid materials. In operation, such apparatus typically includes an ultrasonic transducer that generates a beam of acoustic signals, which is transmitted into the material of interest and is reflected by various gradients or other physical features of the material. The beam may be focused at various depths within the material and may also be scanned so that the reflected acoustic signals may be used to provide image data about various aspects of the material.

In a particular application of ultrasonic systems in the field of medicine, ultrasonic imaging systems are used to examine or monitor the anatomical features of a patient. For example, the reflected signals may be received, analyzed, and processed to produce an image display that is representative of blood flow, tissue, or the structure of internal organs, such as the heart.

In a phased array ultrasound imaging system, an ultrasound transducer includes an array of transducer elements. The system includes a multiple channel transmitter and a multiple channel receiver connected through a transmit/receive switch to the transducer. Each transmitter channel causes a selected transducer array element to transmit an ultrasound pulse into an object being imaged. The transmitted ultrasound energy is steered along a transmit scan line and is focused by applying appropriate delays to the pulses transmitted from each transducer array element, so that the transmitted energy adds constructively a desired focal point to form a transmit beam. A part of the transmitted ultrasound energy is reflected back to the transducer array by various structures that are in the path of the transmitted ultrasound energy.

The reflected ultrasound energy from an object or structure arrives at the array elements at different times. The received signals are amplified and are delayed in separate receiver channels and then are summed in a receive beam former to form a receive beam. The delay for each channel is selected such that the receive beam is steered at a desired angle and is focused at a desired depth. The delays may be varied so as to focus the beam at progressively increasing depths along a receive scan line as the ultrasound energy is received.

Ultrasound energy is transmitted along multiple transmit scan lines in a desired scan pattern, such as a sector scan, and the received signals are processed to produce an image of the region of interest.

In order to obtain the highest quality image, both the transmit beam and the receive beam could be focused at each point in the area being imaged. However, the time required to obtain an image in this manner would be prohibitive. In most prior art systems, the transmit beam is typically focused at a single focal depth, and the receive beam is focused in the scan plane. For both transmit and receive beams, the elevation focus is typically established by means such as an acoustic lens mounted on the transducer. As a result, the transmit beam is out of focus at points displaced from the transmit focal point, and the receive beam is out of focus in the elevation plane, except at a fixed focal point. These factors cause those portions of the image that are displaced from the focal points to be degraded in quality.

A typical elevation-focused transducer in a medical ultrasound imaging system may include an array of 64 to 256 elements. Each transducer element is divided into three or more segments in the elevation plane. The segments of each transducer element can be activated via respective channels in signal processing circuitry for focusing in the scan plane and the elevation plane. A dynamic aperture may also be effected when different active apertures of the transducer are activated by selectively enabling different groups of transducer elements and segments. See, for example, U.S. Pat. No. 5,301,168, assigned to the assignee of the present application, which discloses an ultrasound transducer having rows and columns of transducer elements, and U.S. Pat. No. 5,462,057, assigned to the assignee of the present application, which discloses a phased array ultrasound transducer divided into transducer elements arranged side-by-side in the lateral direction.

However, as the array size increases, the demand for channels will increase as well. For example, a 128-channel system is impractical for use with a 128-element linear array having 256 segments, as a 128-channel system offers an insufficient number of channels to provide both scan plane and elevation focusing.

While features such as high resolution acoustic imaging, electronic beam steering, and electronic focusing provide many advantages, the ultrasonic imaging systems of the prior art that provide such features are becoming more difficult and expensive to construct because of the large number of channels that are required. What is needed is an imaging system for effecting high resolution acoustic imaging with use of a moderate number of signal processing channels to provide beam focusing in the elevation plane.

SUMMARY OF THE INVENTION

The present invention provides an improved ultrasound imaging system suitable for use in varied applications, such as in medicine, non-destructive test and analysis, and in other fields of use.

I have found that when effecting beam focusing at shallow depths, i.e., at short focal lengths, in an ultrasound imaging system, there are certain signal processing channels that are typically not utilized for scan plane focusing and therefore can be allocated to provide elevation plane focusing of certain transducer element segments. As a result, an ultrasound imaging system may be constructed and operated so as to accomplish beam focusing in the elevation plane with use of fewer channels, as compared to imaging systems operated according to the prior art.

According to the present invention, a preferred embodiment of an ultrasound imaging system comprises an array of ultrasound transducer elements, wherein the transducer array is divided into plural transducer elements arranged in the direction of the scan plane and each transducer element is divided into three or more segments in the direction of the elevation plane. The segments of each transducer element can be activated for transmission and reception of ultrasound energy. The system includes activation means for activation of certain ones of the segments of each transducer element for transmission and reception of ultrasound energy, including a transmitter for transmitting a beam of ultrasound energy from the array into a region of interest, and a receiver for receiving a return beam and for generating signals in response; and a signal processing section that employs a plurality of signal processing channels, wherein the signal processing section includes: a signal processing circuit, a beam former, and a controller for effecting signal processing, image display, and system control of various functions. A preferred embodiment of the signal processing section may further include switch means, such as a plurality of electronic switches and multiplexors in an electronic switch circuit, operable under the control of the controller and connected to the transducer array, for allocating the channels with respect to the segments to vary the arrangement of channels applied to selected ones of the transducer segments.

In a particular feature of the invention, the system effects allocation of signal processing channels for focusing in the scan and elevation planes, wherein the allocation is performed according to beam focal length. At a short focal length, certain ones of the channels are allocated to effect focusing in the scan plane. Any channels that heretofore would be unused for scan plane focusing at the short focal length are selectably allocated to effect beam focusing in the elevation plane. As the beam focal length increases from the short focal length, an increasing number of channels are allocated to effect scan plane focusing. Those channels that are not allocated to the scan plane focusing are selectably allocated to certain segments to allow beam focusing in the elevation plane.

The allocation of channels may change during the process of scanning to make the best use of system channels at all points in the image. For example, changes in channel allocation during a transmit mode may be either sequenced or static; changes in channel allocation during a receive mode may be dynamic, sequenced, or static. These allocation schemes are meant to be representative and should not be considered limiting.

Dynamic channel allocation refers to an operating mode wherein changes in the channel allocation can take place during receive mode in a fashion similar to dynamic receive aperture or dynamic receive focus in conventional phased array systems. Sequenced channel allocation refers to an operating mode wherein changes in channel allocation can take place at the beginning of each transmit/receive interval in a multiple zone mode of operation wherein a single image line is formed by splicing several scan lines. Static channel allocation refers to an operating mode wherein at least a complete image is formed with use of a certain channel allocation and wherein further changes to that channel allocation might only occur when an operator makes changes to the imaging system controls.

In one aspect of the invention, both transmit and receive channel allocations may be sequenced such that each image line is formed from two or more ultrasonic scan lines. The first scan line is formed with a transmit focus near the array and with some channels being allocated to elevation focusing and other channels allocated to scan plane focusing. Intermediate scan lines are formed with a transmit focus at intermediate distances that increase from the array and with a corresponding increase in the number of channels allocated to the scan plane, while fewer channels are allocated to the elevation plane focus. A final scan line may be formed with a transmit focus far from the array wherein substantially all channels are allocated to focusing in the scan plane. The multiple scan lines may then be combined, or "spliced", to form a single image line with multiple transmit foci and multiple sets of channel allocations.

In another aspect of the invention, the contemplated system may be operated with a selected channel allocation during transmit mode, wherein the selected channel allocation may be controlled by the location of the transmit focal point and wherein dynamic channel allocation may be implemented during a receive mode. For example, allocation in the receive mode may be combined with a dynamic receive aperture in the scan plane such that the channel allocation is substantially continuously updated during the course of the receive interval.

In a another aspect of the invention, the system may be operated with sequenced channel allocation during transmit mode and dynamic channel allocation during receive mode.

An imaging system constructed according to the present invention offers several advantages.

The ultrasound imaging system may be constructed according to the present invention to provide features such as electronic beam steering and electronic focusing, but with use of fewer channels.

In contrast to the imaging systems of the prior art which typically utilize large numbers of channels and ancillary apparatus to operate a large number of transducer elements, the present invention provides a system for effecting elevation focusing wherein the number of channels may be less than the total number of transducer element segments.

The contemplated imaging system thus advantageously uses dynamic aperture wherein smaller apertures are employed to provide good beam focusing at shorter focal lengths, and full apertures are provided at longer focal lengths.

For a fixed elevation aperture, depth of field increases with increasing focal depth. By appropriate choice of elevation F number, the system's focus capability can be made nearly equivalent to that of a conventional system that effects electronic focusing in the elevation aperture. Further, the contemplated system may be equipped with a fixed focus acoustic lens to determine the elevation plane focus at focal lengths beyond the transition focal length. However, the use of allocation of channels, as taught herein, provides a significant advantage over a conventional fixed focus arrangement that is subject to poor depth of field at short focal lengths. The contemplated imaging system therefore offers a capability for elevation plane focusing at short focal lengths that is substantially equivalent to that offered by a conventional imaging system.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
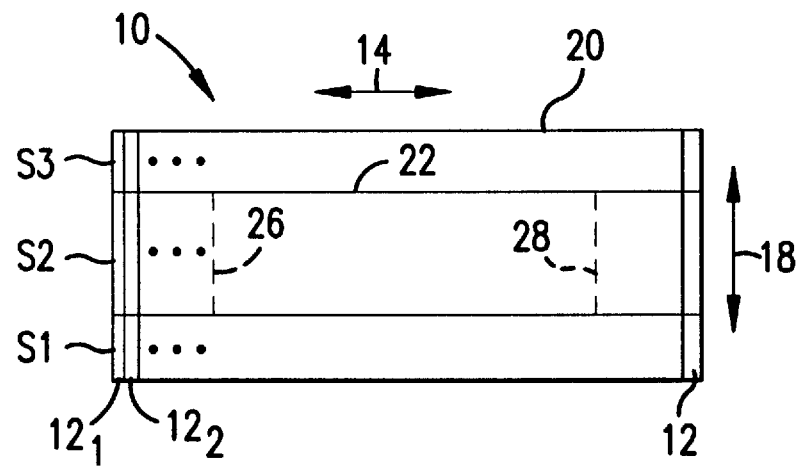
FIG. 1 is a front schematic view of a phased array ultrasound transducer suitable for use in a preferred embodiment of the present invention.

An ultrasound transducer 10 suitable for implementation of the present invention is shown in FIG. 1. The transducer is divided into transducer elements $12_1$, $12_2$, ... $12_N$ arranged side-by-side in the direction 14 of the scan plane. A typical one of such transducer 10 in a medical ultrasound imaging system may include 64 to 256 elements. Each transducer element $12_1$, $12_2$, ... $12_N$ is divided into at least three segments S1, S2, and S3 which are arranged in the direction 18 of the elevation plane. Segments S1 and S3 can be considered respectively as the upper outer and lower outer segments; segments S2 can be considered as middle segments. Each segment S1, S2, S3 of each transducer element $12_1$, $12_2$, ... $12_N$ can be individually activated for transmission and reception of ultrasound energy. In the illustrated embodiment, each of the outer segments S1 and S3 of a particular element are preferably activated in parallel. The illustrated transducer 10 is preferably constructed as a 128-element linear array having 256 segments for use in an imaging system having 128 channels. However, the illustrated transducer 10 is representative of one preferred embodiment and many other embodiments having differing configurations or numbers of channels are contemplated.

Different active apertures of the transducer are activated by selectively enabling different groups of transducer elements and segments. In a preferred embodiment, a first aperture 20 includes all elements and segments of the transducer 10, both in the scan plane and elevation plane. A second aperture 22 includes only certain segments, such as certain ones of the segments S2 of the transducer elements shown in a central portion of the transducer 10 between dashed lines 26 and 28. The first aperture 20 is used for transmitting and receiving ultrasound energy at what may be considered long focal lengths, and the second aperture 22 is used for transmitting and receiving ultrasound energy at what may be considered short focal lengths.

Figure 2:
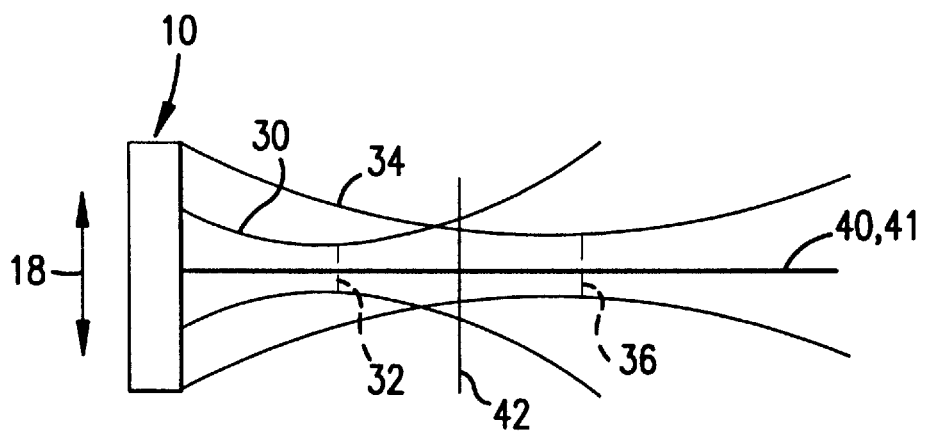
FIG. 2 is a schematic side view of the ultrasound transducer of FIG. 1, illustrating near field and far field beam patterns.
Figure 3:
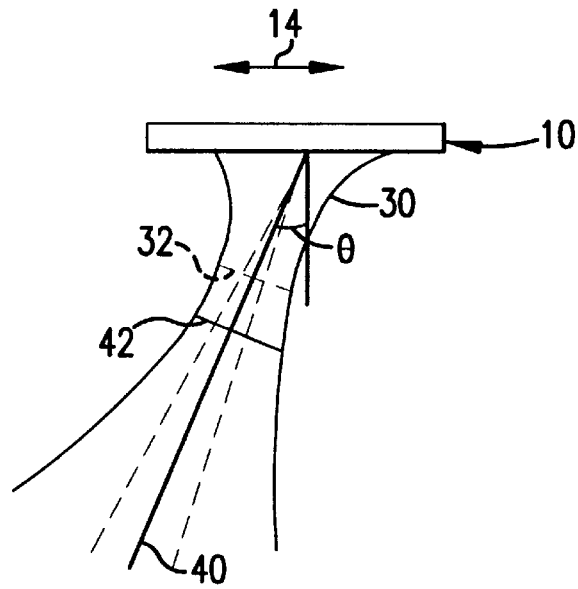
FIG. 3 is a schematic top view of the ultrasound transducer of FIG. 1, illustrating the near field transmitted beam pattern and parallel receive scan lines.
Figure 4:
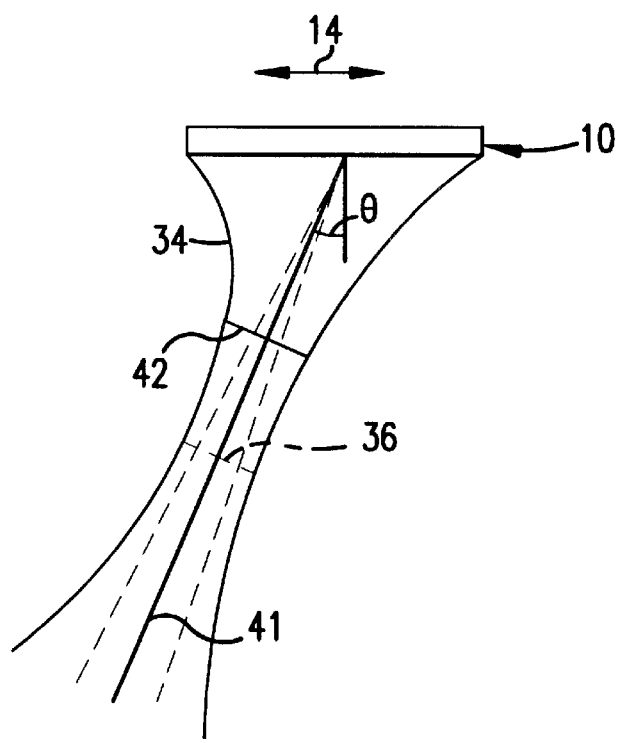
FIG. 4 is a schematic top view of the ultrasound transducer of FIG. 1, illustrating the far field transmitted beam pattern and parallel receive scan lines.

Typical transmit beam patterns for the ultrasound transducer 10 are illustrated in FIGS. 2–4. By appropriately delaying the pulses applied to the transducer elements in the active aperture, as known in the art, the transmitted ultrasound energy is steered in a desired direction with respect to the transducer array and is focused at a desired focal length. A side elevation view of the transducer 10 is shown in FIG. 2. The second aperture 22 transmits ultrasound energy having a beam pattern 30 focused at short focal lengths such as at a focal length 32. The first aperture 20 transmits ultrasound energy having a beam pattern 34 focused at long focal lengths such as focal length 36. Top views of the beam patterns 30 and 34 are shown in FIGS. 3 and 4, respectively. Each beam pattern is preferably steered at an angle (theta) with respect to a normal to the transducer 10. In order to form transmit beam patterns 30 and 34, each transducer element in the active aperture is energized with a pulse having a delay selected to focus the transmitted ultrasound energy at the focal depth 32 or 36 and to steer the transmitted ultrasound energy at the angle (theta). The beam pattern 30 can be represented as a transmit scan line 40, and the beam pattern 34 can be represented as a transmit scan line 41. The transmit scan lines 40 and 41 are co-linear, originate at the center of the active aperture of transducer 10, and have an angle (theta) in the scan plane direction 14 with respect to a normal to transducer 10. The illustrated beam pattern is representative of one preferred embodiment; other embodiments, such as those appropriate for linear arrays and curved linear arrays whereby beam scanning is accomplished by means other than steering, are also contemplated.

The transmitted ultrasound energy produces ultrasound echoes from various structures in the region of interest. The ultrasound echoes are received by the transducer 10 and are converted to electrical signals. By appropriate focusing of the received signals via signal processing on respective signal processing channels in a beamformer, a receive beam is formed. The receive beam is steered in a fashion similar to that described with respect to the transmit beam at a desired steering angle and is dynamically focused at progressively increasing depths as the ultrasound echoes are received, so that the receive beam remains in focus as echoes are received from progressively increasing depths.

With reference to FIG. 3, it can be seen that the beam pattern 30 is focused at a short focal length 32 and the beam pattern 30 is relatively narrow at depths within a region considered as a near field, and wherein the beam pattern 30 is then relatively broad at depths beyond the focal length 32. Conversely, in FIG. 4, beam pattern 34 is focused at a long focal length 42 and the beam pattern 30 is relatively wide at depths within a region considered as the far field. A transition 42 is located between the short and long focal lengths 32 and 36 and may be understood to indicate a transition in the operation of the first aperture 20 and the second aperture 22. Such transition 42 is also representative of a sequenced allocation change in operation between the operation at a short focal lengths, such as focal length 32 and long focal lengths, such as focal length 36. (It will be understood that the illustrated beams 30, 34, focal lengths 32, 36, and transition 42 are merely exemplary and will vary in dimensions depending on the structure of the transducer 10, the implementation of the invention, and so on. The beam patterns shown in FIGS. 3 and 4 may also operated at a plurality of steering angles in the scan plane to form a desired scan pattern, and the channels are processed as described herein to produce signals for generating an image of the region of interest.)

According to a particular aspect of the invention, operation of the transducer 10 includes allocation of channels for electronic focusing of the beam in the elevation plane according to the current beam focal length. Hence, for each beam focal length selected in a range from the shortest focal length at a point proximate the transducer 10, to the transition 42, there is a corresponding allocation of channels to the active ones of the segments S1, S2, S3 in a particular element $12_1$, $12_2$, ... $12_N$.

The preceding discussion is limited to a sequence of only two zones for the purpose of clarity in describing system operation. It should be noted that the preferred embodiment allows two or more zones in the sequence.

Figure 5:
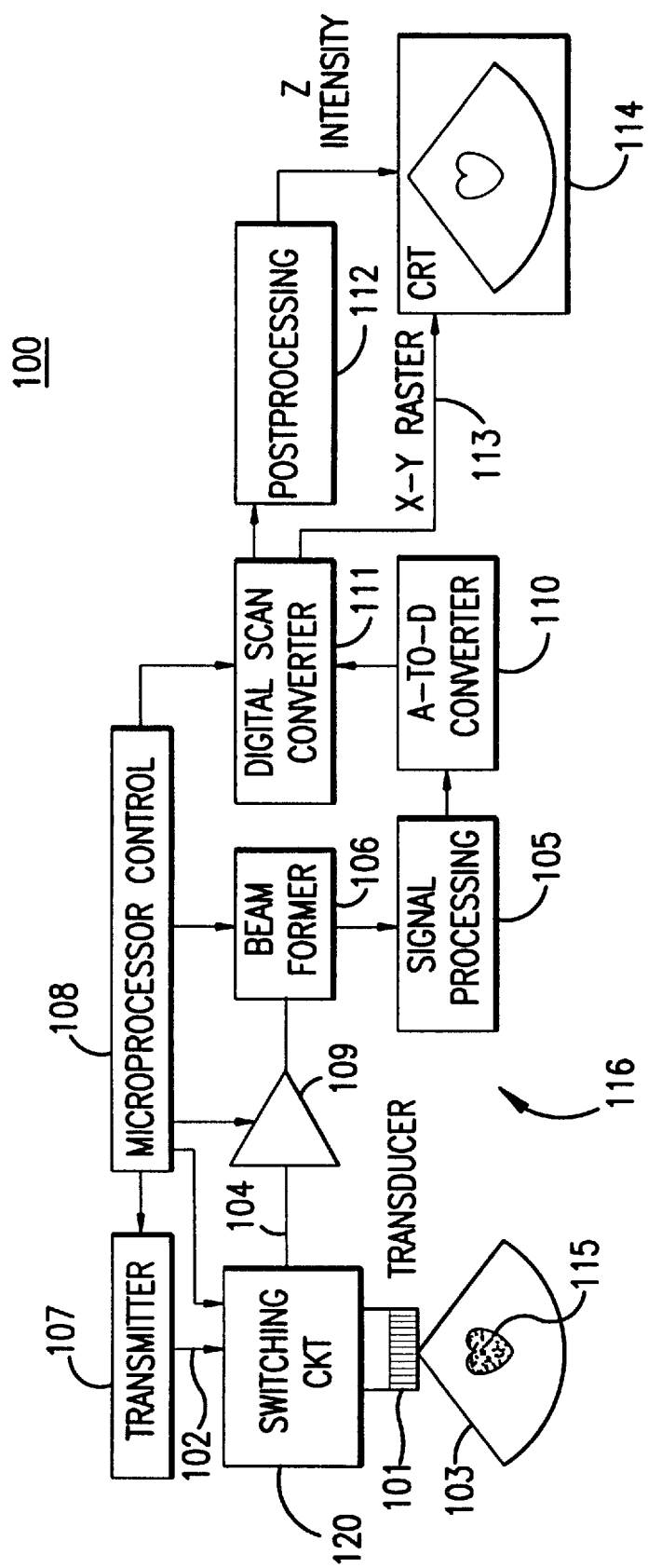
FIG. 5 is a block diagram of an ultrasound imaging system constructed in accordance with the present invention.

As shown in FIG. 5, an ultrasound imaging system 100 may be constructed according to the present invention to provide features such as electronic beam steering and electronic focusing, but with use of fewer channels to effect beam focusing in the elevation plane at short focal lengths. As a result, the present invention provides an ultrasound imaging system providing scan plane and elevation plane focusing for effecting high resolution acoustic imaging while being operated with use of a reduced number of channels.

FIG. 5 shows an ultrasound imaging system 100 in which an electrical stimulus 102, such as a pulse, is provided to an array of transducers 101, causing the transducers to transmit an ultrasonic acoustical wave 103. The ultrasonic wave is transmitted into a region of interest and eventually at least partially reflected by an object in the region of interest. In the illustrated embodiment, the region of interest lies within a human body and the object, is for example, a heart 115. The reflected wave ("echo") is received by the transducer array 101 which produces an electrical current 104 that is indicative of the echo. Various properties of signal 104, such as its amplitude and phase, are then analyzed by a signal processing section to determine information about the object, such as its size, location, and velocity. See for example U.S. Pat. No. 5,060,651, U.S. Pat. No. 5,301,168, and U.S. Pat. No. 5,462,057, the contents of which are incorporated herein by reference.

More specifically, FIG. 5 shows a signal processing section microprocessor 108 for controlling each of a transmitter 107, receiver 109, multichannel beam former 106, switching circuit 120, and digital scan converter 111. The echo signal 104 from transducer array 101 is sent to the preamplifier 109 and then in series to beam former 106, signal processor 105, A/D converter 110, and digital scan converter 111. The z-component of the echo signal is sent to post processor 112, and the resulting z-intensity is displayed on CRT screen 114. The x-y component is sent via x-y raster 113 and displayed on CRT screen 114. Any number of different transmitting and imaging processing techniques may be used.

The array of transducers 101 are generally made of piezoelectric materials, such as lead zirconate titanate (PZT) ceramic. They may also be formed of "composites", in which a piezoelectric ceramic and a polymer are combined for an improved range of properties. Acoustic imaging transducers have also been made of electrostrictive materials, which are highly polarizable by the application of a DC bias voltage. Lead magnesium niobate-lead titanate (PMN-PT) is one example of an electrostrictive ceramic.

In the illustrated system 100, a limited number of channels in the signal processing section are available for effecting signal processing. During operation at a given focal length, certain ones of the channels are allocated to effect scan plane focusing, and this number of channels thus used for scan plane focusing is selected according to the teachings of the prior art, and need not be described further. However, in a departure from the prior art, any of the limited number of channels that are not allocated for effecting scan plane focusing are then allocated by the switching circuit 120 for effecting elevation plane focusing. The limited number of channels thus allocated are then efficiently used to effect signal processing in signal processing circuit 105 so as to allow, when possible, both scan plane focusing and elevation plane focusing. As a result, the overall quality of beam focusing is improved with use of the same or fewer number of beam-forming channels that are employed for effecting beam focusing in systems operated according to the prior art.

In particular, it is contemplated that during system operation at short focal lengths, or typically when the second aperture 22 of FIG. 1 is active, not all of the channels will be necessary for effecting scan plane focusing and hence are available for allocation to effect elevation plane focusing. The contemplated system 100 thus advantageously performs scan plane and elevation plane focusing at, e.g., smaller apertures to provide good overall beam focusing at short focal lengths, while nonetheless providing full apertures during operation at long focal lengths.

In the preferred embodiment, beam focusing is effected such that, when operable at short focal lengths, certain ones of the channels are allocated to scanning in the scan plane and other ones of the channels are allocated to focusing in the elevation plane. As the focal length of the beam increases, more channels are necessary for scan plane focusing, and consequently fewer channels are allocated to effect elevation plane focusing. When substantially all of the channels are allocated to focusing in the scan plan, the beam is subject to fixed focusing in the elevation plane. Fixed elevation plane focusing may be provided as known in the art by, for example, a fixed acoustic lens integrated in the transducer 101.

For example, an embodiment of system 100 may be constructed to include an array 101 having 128 elements that is tuned to 7.5 megahertz (MHZ). The elements may be separated by 0.2 millimeters (mm) and thus provide an image width of 25.6 mm. Each element in the array 101 can be divided into three segments (one inner and two outer segments). With the outer segments connected in parallel, however, the array 101 effectively operates as a total of 256 segments. With a scan plane F number of 1.5, only 64 channels will be required for scan plane focusing in the near field to a depth of 19.2 mm. Assuming the imaging system 100 has 128 channels, the remaining (and heretofore unused) 64 channels can be allocated to focus the outer segments of the array 101 so as to provide both scan plane and elevation plane focusing. At long focal lengths (beyond a transition at 19.2 mm), the outer segments can be switched in parallel with the inner segments, thus providing fixed elevation focus that is determined by a physical beam focusing means such as an acoustic lens integrated in the array 101. The full complement of channels (128 channels) are then available for scan plane focusing to maintain the desired F number in the scan plane to a depth of 25.6 mm. At short focal lengths, electronic focusing is thus achieved in both the scan plane and elevation plane. At long focal lengths, the scan plane is subject to electronic focus and the elevation plane is subject to a fixed focus.

An embodiment of the present invention may be constructed to provide a high resolution acoustic imaging system in which a moderate number of channels (e.g., 128 channels) achieve a degree of resolution at short focal lengths that is substantially equivalent to the resolution provided by a 256 channel system of the prior art.

Preferred embodiments of the system 100 may be understood to provide allocation of a channels with respect to a multiple element array by way of high voltage multiplexor chips in the switching circuit 120 to switch channels to the appropriate element segments.

Preferred embodiments of the system 100 are contemplated as being amenable to inclusion of additional techniques known in the art for improving beam focusing, steering, and aperture control.

Preferred embodiments of the system 100 may be understood to perform beam focusing that may be divided into two or more splice zones. Splicing has the additional benefit of providing multiple transmit focal points and thereby better image uniformity than that of a single splice. In performing beam splicing, two or more transmit beams are transmitted at the same steering angle, but at different focal depths. The received signals in the region of each transmit focal point are "spliced" together to form a single receive line at each steering angle. The transmitted beams are focused both in elevation plane and in scan plane by energizing different apertures of the transducer at different focal depths. Since the spliced receive line is made up of received signals from regions where the transmitted beams are relatively focused, image quality is improved.

Hence, the transducer 10 may be used to transmit ultrasound energy along transmit scan line 40, with the transmitted energy having near field beam pattern 30, as shown in FIG. 3. The signals received in response to the near field beam pattern are stored. Ultrasound energy is transmitted along transmit scan line 41 with the transmitted energy having far field beam pattern 34, as shown in FIG. 4. The signals received in response to the far field beam pattern are also stored. The signals received from beam pattern 30 are combined, or spliced, with the signals received from beam pattern 34. The result is a spliced signal which provides high image quality, both in the near field and in the far field, because all received signals are obtained from regions where the transmitted ultrasound energy is relatively focused. Preferred embodiments may take advantage of beam splicing techniques as disclosed, for example, in U.S. Pat. No. 5,301,168, issued to Miller and assigned to the assignee of the present application, the contents of which are incorporated herein by reference.

Also as disclosed in U.S. Pat. No. 5,462,057, issued to Hunt et al. and assigned to the assignee of the present application, preferred embodiments of system 100 may employ a phased array ultrasound imaging system wherein a high quality image is obtained by a combination of line splicing and parallel receive beam forming. In particular, the array 101 may include at least two selectable elevation apertures. The transmitter 107 includes means for transmitting ultrasound energy along the near field transmit scan line with a first elevation aperture and for transmitting ultrasound energy along the far field transmit scan line with a second elevation aperture that is larger than the first elevation aperture. The signal processing section includes receiver means for receiving signals along the first and second near field receive scan lines with the first elevation aperture and for receiving signals along the first and second far field receive scan lines with the second elevation aperture. Thus, ultrasound energy transmitted along the near field and far field transmit scan lines is focused, both in the scan plane and in the elevation plane. The receiver means includes means for varying the receive angle during reception of the ultrasound echoes to compensate for spatial variations in the transmitted ultrasound energy.

While this invention has been particularly shown and described with references to preferred embodiments thereof it will be understood by those skilled in the art that various changes in form and details may be made therein without departing from the spirit and scope of the invention as defined by the appended claims.

What is claimed is:

1. An ultrasound imaging system for effecting beam focusing in a scan plane and in an elevation plane, comprising:

an array of ultrasound transducer elements, wherein the plural transducer elements are arranged in the direction of the scan plane and each transducer element is divided into three or more segments in the direction of the elevation plane;

activation means for activation of certain ones of the segments of each transducer element for transmission and reception of ultrasound energy, including a transmitter for transmitting a beam of ultrasound energy from the array into a region of interest, and a receiver for receiving a return beam and for generating signals in response;

a signal processing section that employs a plurality of signal processing channels, wherein the section includes: a signal processing circuit, a beam former and associated circuits for effecting signal processing and image display, and a controller for effecting system control and allocation of the signal processing channels to the plural transducer elements for focusing in the scan and elevation planes; wherein channel allocation is performed according to beam focal length, and wherein at least one of the channels not allocated to effect scan plane focusing is thereby selectably allocated to effect beam focusing in the elevation plane.

2. The imaging system of claim 1, wherein the activation means further comprises an electronic switch circuit connected to the transducer array and operable under the control of the signal processing section for effecting the channel allocation.

3. The imaging system of claim 1, wherein the transducer array includes an acoustic lens for effecting a fixed focusing of the received beam in the elevation plane.

4. The imaging system of claim 1, wherein the channel allocation is provided to effect beam focusing in at least a first splice zone and a second splice zone.

5. The imaging system of claim 1, wherein signal processing section includes means for effecting a dynamic aperture, and wherein channel allocation is provided according to the dynamic aperture.

6. The imaging system of claim 1, wherein the transducer array is provided in the form of a linear array of piezoelectric transducer elements.

7. The imaging system of claim 1, wherein the transducer array is provided in the form of a curved linear array of piezoelectric transducer elements.

8. The imaging system of claim 1, wherein the transducer array is provided in the form of a matrixed array of piezoelectric transducer elements.

9. The imaging system of claim 1, wherein the number of beam-forming channels is less than the total number of active transducer segments.

10. The imaging system of claim 1, wherein the allocation of channels for transmit beam focusing is effected in at least one mode selected from the group consisting of sequenced channel allocation mode and static channel allocation mode while receive beam focusing is effected in at least one mode selected from the group consisting of dynamic channel allocation mode, sequenced channel allocation mode, and static channel allocation mode.

* * * * *